US011165993B2

(12) United States Patent
Lee

(10) Patent No.: US 11,165,993 B2
(45) Date of Patent: Nov. 2, 2021

(54) CONTACT AREA DIFFUSION FACTOR FOR QUANTIFYING FAT CONTENTS OF LIQUID

(71) Applicant: Femtobiomed Inc., Seongnam-si (KR)

(72) Inventor: Sanghyun Lee, Seongnam-si (KR)

(73) Assignee: Femtobiomed Inc., Seoul (KR)

(*) Notice: Subject to any disclaimer, the term of this patent is extended or adjusted under 35 U.S.C. 154(b) by 257 days.

(21) Appl. No.: 15/962,626

(22) Filed: Apr. 25, 2018

(65) Prior Publication Data

US 2018/0241971 A1    Aug. 23, 2018

Related U.S. Application Data

(60) Continuation-in-part of application No. 15/482,370, filed on Apr. 7, 2017, now abandoned, which is a division of application No. 14/106,992, filed on Dec. 16, 2013, now abandoned.

(30) Foreign Application Priority Data

Dec. 17, 2012  (KR) .................. 10-2012-0147029
Apr. 26, 2017  (KR) .................. 10-2017-0053956
Apr. 26, 2017  (KR) .................. 10-2017-0053957

(51) Int. Cl.
| | |
|---|---|
| A61B 5/00 | (2006.01) |
| G06K 9/00 | (2006.01) |
| G06T 7/00 | (2017.01) |
| H04N 7/18 | (2006.01) |
| H04N 5/232 | (2006.01) |
| G06T 7/62 | (2017.01) |
| G06K 9/52 | (2006.01) |
| G01N 33/487 | (2006.01) |
| A61B 5/145 | (2006.01) |
| A61B 5/20 | (2006.01) |

(52) U.S. Cl.
CPC ........... *H04N 7/18* (2013.01); *A61B 5/14507* (2013.01); *A61B 5/208* (2013.01); *A61B 5/4064* (2013.01); *A61B 5/4082* (2013.01); *A61B 5/4088* (2013.01); *A61B 5/7275* (2013.01); *G01N 33/487* (2013.01); *G06K 9/52* (2013.01); *G06T 7/0012* (2013.01); *G06T 7/62* (2017.01); *H04N 5/23296* (2013.01); *A61B 5/0077* (2013.01); *A61B 5/14517* (2013.01)

(58) Field of Classification Search
CPC .................................... G06K 9/52; G06T 7/62
See application file for complete search history.

(56) References Cited

U.S. PATENT DOCUMENTS

| | | |
|---|---|---|
| 6,278,008 B1 | 8/2001 | Endo et al. |
| 6,330,350 B1 | 12/2001 | Ahn et al. |
| 6,845,654 B2 | 1/2005 | Kinnunen et al. |
| 7,952,698 B2 | 5/2011 | Friedrich et al. |
| 9,993,403 B2 | 6/2018 | Ranade et al. |
| 2008/0038762 A1 | 2/2008 | Troup |
| 2009/0299172 A1 | 12/2009 | Corot et al. |
| 2013/0167621 A1 | 7/2013 | Lin et al. |
| 2014/0169646 A1 | 6/2014 | Lee |
| 2015/0118696 A1 | 4/2015 | Haselton et al. |
| 2016/0080696 A1 | 3/2016 | Lee |

FOREIGN PATENT DOCUMENTS

| | | |
|---|---|---|
| CN | 161193 A | 5/2005 |
| CN | 102175578 A | 9/2011 |
| EP | 3104160 A1 | 12/2016 |
| JP | 09-194683 A | 7/1997 |
| JP | H11-304685 A | 11/1999 |
| JP | 2004-520580 A | 7/2004 |
| JP | 2006-056802 | 3/2006 |
| JP | 2008-249332 A | 10/2008 |
| JP | 2009-162759 A | 7/2009 |
| JP | 2011-507865 A | 3/2011 |
| JP | 4958272 B2 | 6/2012 |
| JP | 2017-508141 A | 3/2017 |
| KR | 1019950001300 | 1/1995 |
| KR | 10-1997-0005501 B1 | 4/1997 |
| KR | 10-1998-0084281 A | 12/1998 |
| KR | 10-2009-0097102 A | 9/2009 |
| KR | 10-1361072 | 2/2014 |
| KR | 10-2014-0055342 A | 5/2014 |
| KR | 10-2016-0148519 A | 12/2016 |
| RU | 1791756 C | 1/1993 |
| WO | WO 94/23280 | 10/1994 |
| WO | WO 2013/0176757 A1 | 11/2013 |
| WO | WO 2015/119314 A1 | 8/2015 |

OTHER PUBLICATIONS

CN Office Action issued in CN201480074870.1, dated Jun. 27, 2018, 6 pages.
International Search Report issued in PCT/KR2014/001077, dated Nov. 26, 2014, and English translation, 5 pages.
Gao, Xiu-yun, et al., Research on Surface Properties of Fluorinated Acrylate Copolymer Latex, Leather and Chemicals, Apr. 2013, 8 pages.
International Search Report for Application No. PCT/KR2018/004808, dated Aug. 8, 2018, 3 pages.
Japanese Office action for Application No. 2018-566952, dated Oct. 7, 2019, 3 pages.
Japanese Office action for Application No. 2018-068574, dated Mar. 5, 2019, 4 pages.
Choi et al., "Droplet Evaporation of Pure Water and Protein Solution on Nanostructured Superhydrophobic Surfaces of Varying Heights," Langmuir, 25(13): 7561-7567, 2009.

(Continued)

*Primary Examiner* — Christopher Adam Hixson
(74) *Attorney, Agent, or Firm* — Lewis Roca Rothgerber Christie LLP

(57) ABSTRACT

A method for quantifying a content of hydrophobic components contained in a liquid using a contact area diffusion factor (CADF) of a droplet of the liquid to a solid surface is provided. In addition, the obtained content of the hydrophobic components provides information about prediction for possibility of developing a metabolic disease or dementia, or information about the incidence or progression of a metabolic disease or dementia.

5 Claims, 4 Drawing Sheets

(56) References Cited

OTHER PUBLICATIONS

Itaya et al., "Colorimetric determination of free fatty acids in biological fluids," Journal of Lipid Research, 5 pages, 2017.
Liu et al., "Evaporation of sessile water/ethanol drops in a controlled environment," Phys. Chem. Chem. Phys., 10:7150-7157, 2008.
Mathcentre, "Substitution & Forulae." pp. 1-10, (www.mathcentre.ac.uk), (mathcentre 2009).
Park et al., "How the change of contact angle occurs for an evaporating droplet: effect of impurity and attached water films," Soft Matter, 8: 11889-11896, 2012.
Tallis et al., "Lipoprotein profiling by high performance gel chromatography," Clinica Chimica Acta 228:171-179, 1994.
Wilson et al., "Free Fatty Acids Stimulate the Polymerization of Tau and Amyloid beta Peptides," American Journal of Pathology, vol. 150, No. 6, Jun. 1997, pp. 2181-2195.
Grant of Patent for Korean Patent Application No. 10-2018-0048007, dated Feb. 14, 20120, 3 pages.

CONTACT AREA DIFFUSION FACTOR FOR QUANTIFYING FAT CONTENTS OF LIQUID

CROSS-REFERENCE TO RELATED APPLICATIONS

This application is a Continuation-In-Part of U.S. Ser. No. 15/482,370, filed Apr. 7, 2017 (a Divisional of U.S. patent application Ser. No. 14/106,992, filed Dec. 16, 2013), which claims priority to Korea Patent Application No. 10-2012-0147029, filed Dec. 17, 2012, Korea Patent Application No. 10-2017-0053956, filed Apr. 26, 2017, and Korea Patent Application No. 10-2017-0053957, filed Apr. 26, 2017, the disclosures of which are incorporated herein by reference.

BACKGROUND

1. Field

The present invention relates to a method for quantifying the content of hydrophobic components, e.g., fat components contained in a liquid from the Contact Area Diffusion Factor (CADF) value of the liquid droplet. The present invention also relates to a method for providing information about prediction of the possibility of developing a metabolic disease or dementia, e.g., diabetes, fat emboliform, or dementia, or information on diagnosing the incidence or progression of these diseases using said method for quantifying the content of the hydrophobic components.

2. Description of the Related Art

The social costs of dementia are higher than the total cost of cancer, heart disease and stroke, and the dementia-related healthcare expenditure is expected to double every decade. According to a report in the New England Journal of Medicine, one of the most prestigious peer-reviewed medical journal published by Massachusetts Medical Society, the annual cost of Alzheimer's and related diseases to patients' family and society is estimated at about 157 billion USD, and the annual cost of treatment for a dementia patient is estimated to be 56,000 USD per person. 5.3 million Americans have Alzheimer's disease, the most common symptom of dementia, which is now the sixth leading cause of death in the United States.

However, in spite of expensive dementia treatment costs, it is impossible to completely cure the dementia at present and the symptoms can only be temporarily relieved with the current level of technology, and it is even difficult to delay the progress of the disease. This is because of the lack of understanding in the definite pathological cause of dementia and personalized treatment according to individual patient's differences. The personalized dementia treatment begins when a convenient diagnosis of dementia is available to patients at low cost in daily life, and with the management of the individual's treatment, it can be a great help to prevent the increase of dementia patients and the increase of the related cost.

FES (fat embolism syndrome) is one of the major causes of death in surgical procedures. In particular, liposuction and orthopedic surgery, which are performed very often per year, have the low probability of FES. However, due to the high mortality rate at the onset of FES, a large number of deaths occur every year during liposuctions and orthopedic surgeries.

According to the 2009 report of the International Society for Aesthetic Plastic Surgery (ISAPS), liposuction is a plastic operation (surgery) which is the most frequently performed among 21 categories of plastic surgery, and over 1.6 million liposuctions were performed over the world.

Although liposuction is the most frequently-performed operation among plastic operations, risks that occur during liposuction are not well-known to the public. FES would occur by fats passing into damaged blood vessels during liposuction, and may seriously deteriorate the function of the lung or penetrate into other organs. Despite the relatively low incidence of FES, it is known that hundreds of deaths occur worldwide due to its very high mortality.

Therefore, in order to prevent FES during liposuction, it is necessary to measure the amount of fats passed into blood vessels before, during and after an operation. However, there are no apparatuses for quantifying the content of fats passed into blood vessels.

The present inventor has completed the present invention by confirming that the fat content of liquid may be measured from the CADF (contact area diffusion factor) values of a liquid droplet.

SUMMARY

The object of the present invention is to provide a method for quantifying the content of hydrophobic components, e.g., fat components contained in a liquid from the CADF value of the liquid droplet. Further, the object of the present invention is to provide a method for providing information about prediction of the possibility of developing dementia or metabolic diseases such as diabetes, or fat emboliform, or information on diagnosing the incidence or progression of these diseases using said method for quantifying the content of the hydrophobic components.

Embodiments are directed to a method for quantifying a content of hydrophobic components contained in a liquid.

The embodiments may be realized by conducting following steps: (a) contacting a droplet of the liquid to a solid surface and measuring an initial contact area ($A_0$) and an initial contact diameter ($d_0$) of a contact surface between the droplet and the solid surface; (b) after the lapse of predetermined time (t), measuring a contact area ($A_t$) and a contact diameter ($d_t$) of the contact surface between the droplet and the solid surface; and (c) obtaining a contact area diffusion factor (CADF) according to the following Equation 1:

$$CADF = \left(\frac{A_t^n - A_0^n}{A_0^n}\right)^N + \left(\frac{d_t^m - d_0^m}{d_0^m}\right)^M \quad \text{(Equation 1)}$$

wherein n, m, N and M are constants; and (d) obtaining the content of the hydrophobic components contained in the droplet by using the contact area diffusion factor (CADF) and the following Equation 2:

$$C_{CADF}(\mu g/ml) = kCADF + C_0 + Ae^{\frac{CADF-Q}{P}} + B\log_D CADF \quad \text{(Equation 2)}$$

wherein k, $C_0$, A, B, D, P and Q are correction constants.

The liquid may be a body fluid.

The body fluid may be selected from the group consisting of blood, serum, plasma, sweat and urine.

The hydrophobic components may be a fat.

Other embodiments are directed to method for providing information about prediction of possibility of developing a metabolic disease or dementia, or information about incidence or progression of the metabolic disease or the dementia The embodiments may be realized by conducting following steps: (a) contacting a droplet of a body fluid from a subject to a solid surface and measuring an initial contact area ($A_0$) and an initial contact diameter ($d_0$) of a contact surface between the droplet and the solid surface; (b) after the lapse of predetermined time (t), measuring a contact area ($A_t$) and a contact diameter ($d_t$) of the contact surface between the droplet and the solid surface; (c) obtaining a contact area diffusion factor (CADF) according to the following Equation 1:

$$CADF = \left(\frac{A_t^n - A_0^n}{A_0^n}\right)^N + \left(\frac{d_t^m - d_0^m}{d_0^m}\right)^M \quad \text{(Equation 1)}$$

wherein n, m, N and M are constants,
(d) obtaining the content of fat component contained in the droplet by using the contact area diffusion factor (CADF) and the following Equation 2:

$$C_{CADF}(\mu g/ml) = kCADF + C_0 + Ae^{\frac{CADF-Q}{P}} + B\log_D CADF \quad \text{(Equation 2)}$$

wherein k, $C_0$, A, B, D, P and Q are correction constants; and (e) comparing the obtained content of the fat component with a content of a fat component obtained from a body fluid of a normal person.

It may be determined that the possibility of developing the metabolic disease or dementia is high or the incidence of the metabolic disease or dementia may be diagnosed when a value obtained by subtracting the content of the fat component from the subject from the content of the fat component obtained from the normal person is positive.

The body fluid may be selected from the group consisting of blood, serum, plasma, sweat and urine.

The metabolic disease may be selected from the group consisting of diabetes and fat embolism.

The dementia may be selected from the group consisting of Alzheimer's disease, Parkinson's disease, vascular dementia, mixed dementia and mild cognitive disorder.

BRIEF DESCRIPTION OF THE DRAWINGS

Features will be apparent to those of skill in the art by describing in detail exemplary embodiments with reference to the attached drawings in which.

DETAILED DESCRIPTION

Example embodiments will now be described more fully hereinafter with reference to the accompanying drawings; however, they may be embodied in different forms and should not be construed as limited to the embodiments set forth herein.

A method for quantifying hydrophobic components contained in a liquid according to one embodiment of the present invention provides calculating the CADF (contact area diffusion factor) for the contact surface which appears when the liquid droplet contacts the solid surface, and quantifying the hydrophilic component, e.g., the fat component, contained in a liquid on the basis of the CADF value calculated above.

The principle of the quantification is as follows.

Figure 1:
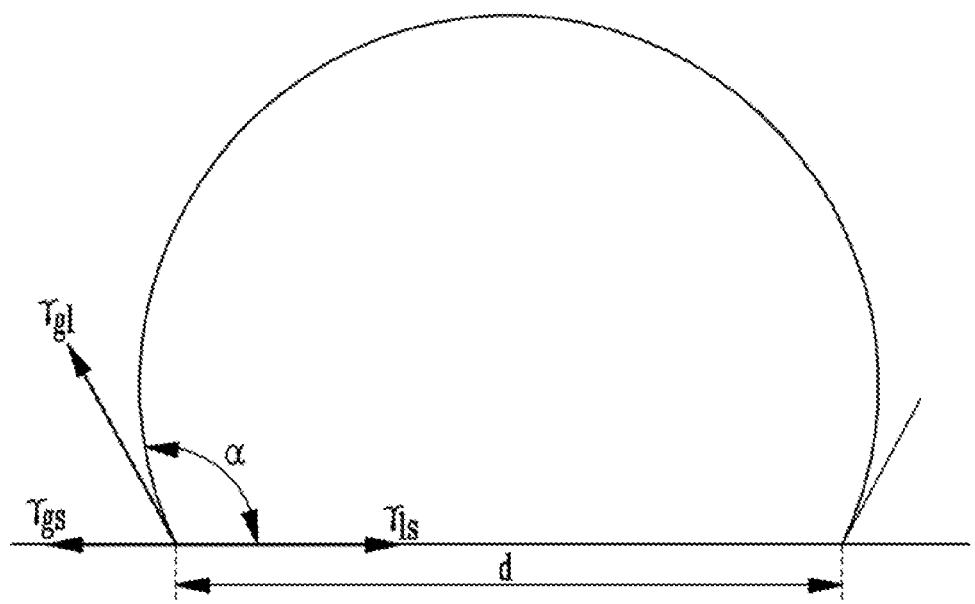
FIG. 1 illustrates three surface tensions acting along the contact line between a droplet and a solid surface.

Referring to FIG. 1, $\gamma_{gi}$ is a surface tension between gas and liquid, $\gamma_{ls}$ is a surface tension between liquid and solid surface, and $\gamma_{gs}$ is a surface tension between gas and solid surface. In addition, $\alpha$ is a contact angle of the droplet, and d is a contact diameter between the droplet and the solid surface.

When the droplet contacts the solid surface, the three surface tensions are balanced with each other. Since the evaporation of a volatile component such as water from the droplet may occur over time, the contact area with the solid surface may decrease as the volume of droplet decreases. Therefore, the contact area of the droplet in contact with the solid surface may be constant or decrease with time, and the contact area may hardly increase.

However, if the balance between the three surface tensions mentioned above is broken, the contact area expansion may occur. Examples are aqueous droplets containing a fat component. A fat component is generally not mixed with water, but in small amounts it can be evenly mixed with water. Some fat components may be dissolved in water in small amounts and may be stably mixed in water in colloidal form. When the fat component is dissolved in the aqueous fluid and the fluid is brought into contact with the solid surface in the form of a droplet, the oil component may stick to the surface of the solid surface, and the balance of the three surface tensions described above may be broken.

The surface tension of water is generally stronger than that of hydrophobic or lipophilic substances. Therefore, when the hydrophobic component dissolved in the aqueous fluid adheres to the solid surface, the balance of the three surface tensions may be broken and the contact area of the droplet may be increased. The amount of the hydrophobic component, e.g., the fat component, attached to the solid surface may be proportional to the fat concentration in the aqueous fluid and the surface adsorption force.

When an aqueous droplet containing fat components which are hydrophobic components is brought into contact with the hydrophobic surface, the hydrophobic components (fat component) may hardly be attached to the solid surface initially. However, as time passes, the hydrophobic component such as the fat component may stick to the hydrophobic solid surface, and the surface tension between the liquid and the solid surface may be changed. Thereby, contact area diffusion (CAD) between the droplet and the solid surface may be developed.

A method for quantifying hydrophobic components contained in a liquid according to one embodiment may comprise the following steps for calculating the CADF:

(a) contacting a droplet, specifically micro-droplet, of the liquid to a solid surface and measuring an initial contact area ($A_0$) and an initial contact diameter ($d_0$) of the contact surface between the droplet and the solid surface;

(b) after the lapse of predetermined time (t), measuring a contact area ($A_t$) and a contact diameter ($d_t$) of the contact surface between the droplet and the solid surface; and (c) obtaining a CADF according to the following Equation 1:

$$CADF = \left(\frac{A_t^n - A_0^n}{A_0^n}\right)^N + \left(\frac{d_t^m - d_0^m}{d_0^m}\right)^M \quad \text{(Equation 1)}$$

wherein n, m, N and M are constants.

The above Equation 1 is a dimensionless equation for the CADF. In the Equation 1, $A_t$ is a contact area of the droplet measured after the lapse of the predetermined time (t), and $A_0$ is an initial contact area. In addition, $d_t$ is a contact diameter measured after the lapse of the predetermined time (t), and $d_0$ is an initial contact diameter.

In Equation 1, the constants n and m may be determined according to the sensitivity of the contact area and the contact diameter of the contact surface to the CADF, respectively. The constants N and M may be determined on the basis of the dependency of a change ratio in the contact area and the contact diameter with respect to the CADF, respectively. Each constant may vary depending on measurement conditions of the CADF.

The higher the content (concentration) of the hydrophobic components, such as the fat components, contained in the droplet, the larger the CADF. Therefore, it is possible to quantify the content of the fat components using the CADF according to one embodiment.

The method for quantifying hydrophobic components contained in the liquid using the CADF obtained above may further comprise following content calculating step:

(d) obtaining the content of the hydrophobic components contained in the droplet by using the CADF and the following Equation 2:

$$C_{CADF}(\mu g/ml) = kCADF + C_0 + Ae^{\frac{CADF-Q}{P}} + B\log_D CADF \quad \text{(Equation 2)}$$

wherein k, $C_0$, A, B, D, P and Q are correction constants.

The correction constants are determined so as to minimize the error in the estimation data of the same by the CADF through comparison correction based on actual data of the fat component contents.

As used herein, the term 'liquid' may refer to a subject material having a volume but not fixed. The liquid may be a body fluid present in the body of an animal including a human. As used herein, the term 'body fluid(s)' may mean blood, serum, plasma, sweat, urine or the like of a human or an animal, but is not limited thereto.

As used herein, the term 'hydrophobic component(s)' or 'lipophilic component(s)' may refer to a component having a low affinity to water, which may not be polarized. The hydrophobic component may not be volatilized in air, but may be a component that affects the properties of the liquid, such as surface tension. The hydrophobic component may be a fat component.

As used herein, the term 'fat (component)' may refer to solid fats, liquid fats, fatty acids, and the like. For example, the solid or liquid fats may include, but is not limited to, rearranged or randomized fats, ester-exchanged fats, and fatty acid triglycerides that occur naturally in vegetable or animal fats. For example, the fatty acid may comprise saturated or unsaturated (mono-, di- or polyunsaturated) carboxylic acid having 10 to 22 carbon atoms, for example 12 to 24 carbon atoms. For example, the saturated fatty acid may include, but is not limited to, capric acid, lauric acid, myristic acid, palmitic acid, stearic acid, or behenic acid. For example, the unsaturated fatty acid may include, but is not limited to, oleic acid, linoleic acid, or erucic acids.

As used herein, the term 'trans fat(s)' may refer to an unsaturated fat containing trans fatty acids. The trans fat may increase the content of LDL cholesterol, while decreasing the content of HDL cholesterol in blood. As used herein, the term 'trans fatty acid' may refer to a fatty acid that is commonly produced by the partial hydrogenation of the unsaturated fatty acid vegetable oils, where the term 'trans' may refer to the opposed positioning of hydrogen atoms when unsaturated fats are partially hydrogenated.

As used herein, the term 'solid(s)' may refer to a solid having at least a certain level of a parallel surface where the droplet can be placed. The solid may be a hydrophobic or water repellant solid, e.g., Teflon, but is not limited thereto. The hydrophobic component, such as fat, may adhere well to the hydrophobic surfaces, so that the sensitivity of the CADF measurement may be increased remarkably. For example, in one embodiment, when using a Teflon plate as a solid, a detection resolution of 1 ppm can be obtained.

As used herein, the term 'contact area ($A_0$, $A_t$)' of a droplet may refer to the area of the portion where the liquid and the solid surface merge into each other. The contact area of the droplet may be measured by using a sensor provided on the solid surface or by calculating the area of the contact surface using an image taken in one direction, e.g., in the downward direction, but is not limited thereto.

As used herein, the term 'contact diameter ($d_0$, $d_t$)' of a droplet may refer to the length of the portion where the liquid and the solid surface merge into each other, which may be observed in any direction. The contact diameter of the droplet may be measured by using a sensor provided on the solid surface or by calculating the length of the contact diameter using an image taken in one direction, e.g., from the side, but is not limited thereto.

As used herein, the term 'contact angle (α)' may refer to an angle formed between the solid surface and the tangent line to the droplet radius from the contact point.

As used herein, the term 'predetermined time (t)' may refer to a time sufficient to generate a contact area diffusion (CAD) phenomenon between the droplet and the solid surface. The predetermined time (t) may be from 5 mins. to 1 hour, for example, from 10 mins. to 30 mins., for example, 20 mins. The predetermined time (t) may be adjusted according to measurement conditions such as fat concentration, temperature, humidity, and the like.

Figure 2:
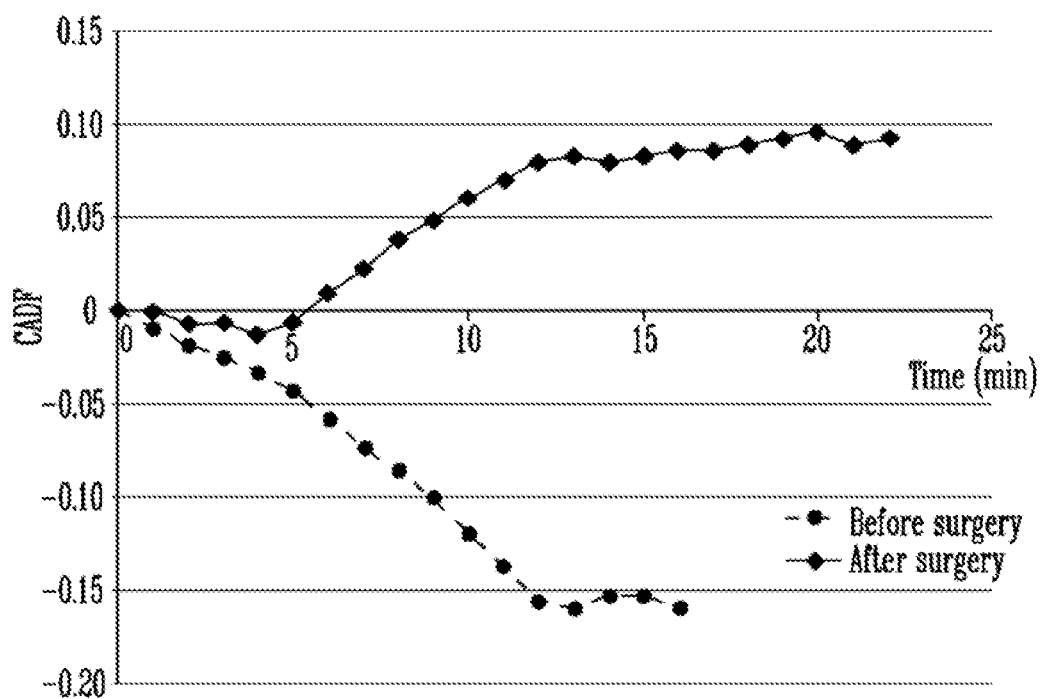
FIG. 2 is a graph that shows the CADF values of the urine before liposuction (without fats) and the urine after liposuction (containing fats).

FIG. 2 is a graph that shows the CADF values of the urine before liposuction (without fats) and the urine after liposuction (containing fats). The horizontal axis represents elapsed time (min.) and the vertical axis represents the CADF value.

Referring to FIG. 2, the CADF value was negative when the fat component was not contained in the urine, while the CADF value was positive when the fat component was contained in the urine, in response to the content of fat components in the urine. It was confirmed that it is possible to detect the content of the fat component contained in a liquid using the above.

The CADF values of the urine without fat components were measured as negative. That is, since the contact angle was maintained, the contact area and/or the contact diameter of the urine droplets without fat components decrease as the water evaporates. In contrast, the CADF values of the urine containing fat components were measured as positive. That is, after a predetermined time elapses, the contact area and/or the contact diameter of the urine droplet became larger than the initial droplet.

Figure 3:
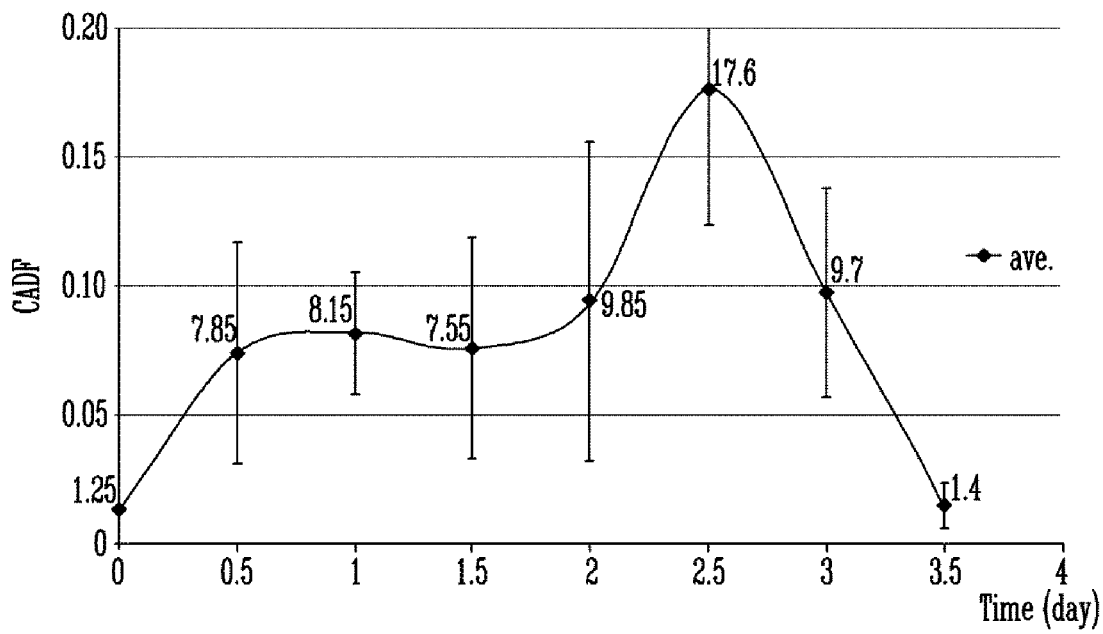
FIG. 3 illustrates the CADF values of the urine samples collected each 0.5 days after liposuction.

FIG. 3 illustrates the CADF values of the urine samples collected every 0.5 days after liposuction. The mean and standard deviation were calculated by measuring the CADF values four times per sample.

Referring to FIG. 3, the CADF of the urine sample collected 2.5 days after the liposuction was the largest, and became negative after 3.5 days. This was consistent with the fact that a patient recovers after an average of three days after liposuction. It was also clear that the sensitivity of the fatty acid content measurement in the urine was high enough so that the effects of medical treatments such as compression bandages and infusion were shown in CADF values.

Figure 4:
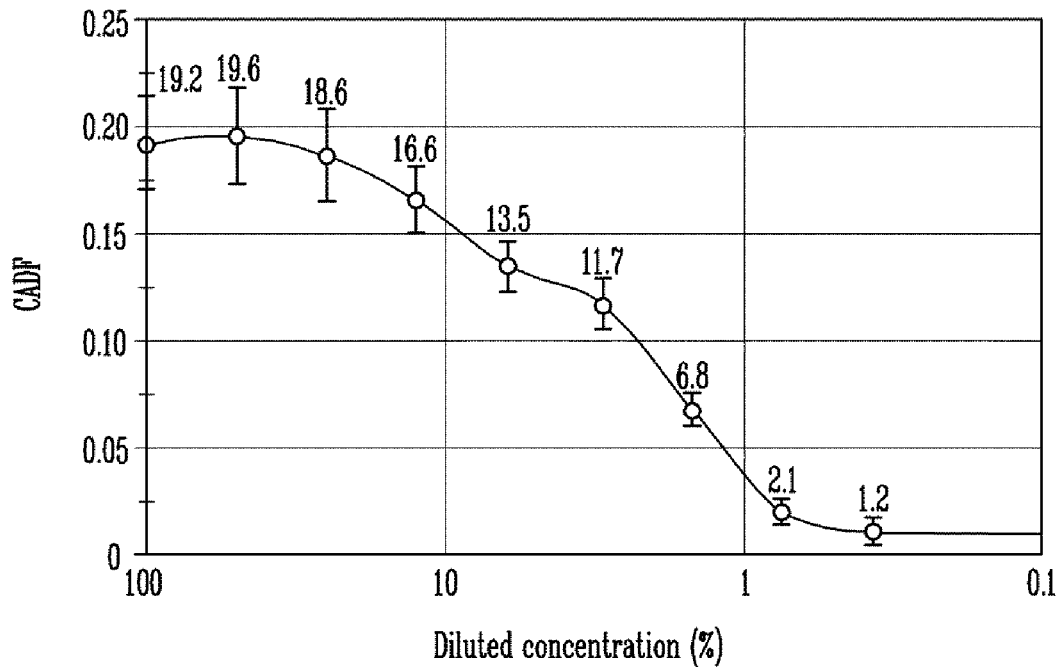
FIG. 4 is a graph showing the relationship between the concentration of the fat component and the CADF values, obtained by diluting the urine sample containing the fat component after the liposuction stepwise with ultrapure water to change the fat component concentration.

FIG. 4 is a graph showing the relationship between the concentration of the fat component and the CADF values, obtained by diluting the urine sample containing the fat components after the liposuction stepwise with ultrapure water to change the fat component concentration.

Urine samples containing fat components collected from liposuction patients were diluted with ultrapure water to a relative concentration ranging from 100% (pure urine) to 0.4%. As the relative concentration decreased, the CADF also decreased, indicating a monotone proportional relationship. Accordingly, it was confirmed that the CADF values can be used for quantifying the fat concentration.

Figure 5:
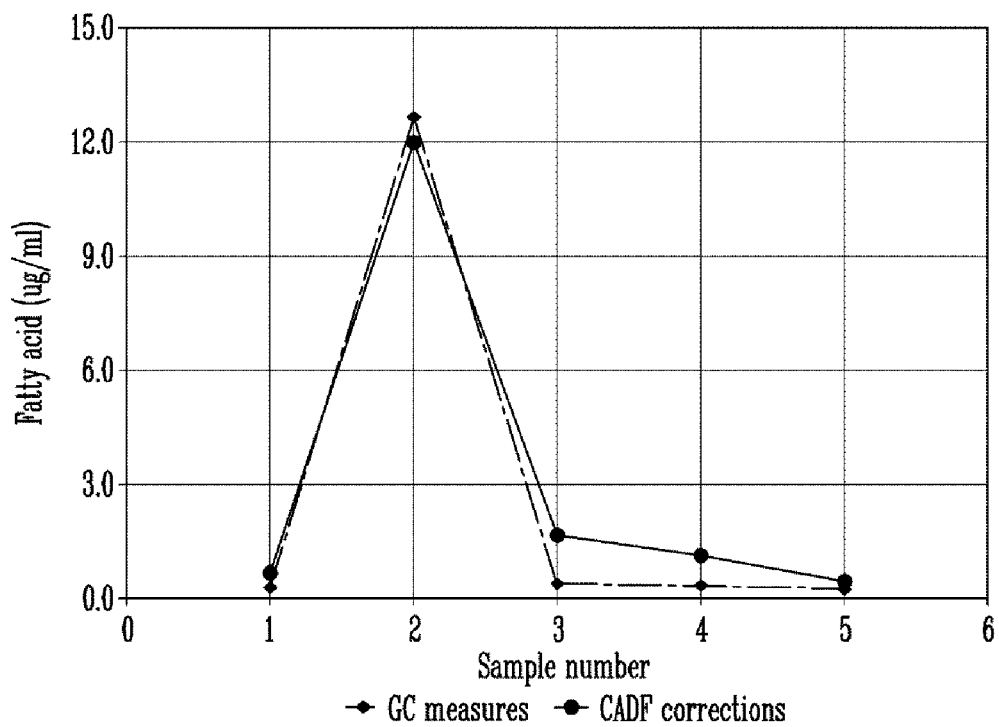
FIG. 5 is a graph comparing the total fatty acids concentration measured by gas chromatography (GC), and the fatty acids concentration obtained by corrected fatty acids concentration conversion equation related to the measured CADF values.

FIG. 5 is a graph comparing the total fatty acids concentration measured by gas chromatography (GC), and the fatty acids concentration obtained by corrected fatty acids concentration conversion equation related to the measured CADF values.

Considering that the CADF according to one embodiment measured the change of the surface energy due to the adsorption of fat on the solid surface, the CADF and the content of the fat component are monotonously proportional. Therefore, the concentration of the fat content was formulated by using a monotone function such as exponential function, linear function, logarithmic function or a combination thereof, as shown in Equation 2 below:

$$C_{CADF}(\mu g/ml) = kCADF + C_0 + Ae^{\frac{CADF-Q}{P}} + B\log_D CADF. \quad \text{(Equation 2)}$$

By applying the fat concentration value measured by the GC method to Equation 2, the correction coefficients were able to be determined and expressed as a simple monotone increasing exponential function as shown in Equation 3 below:

$$C_{CADF} = Ae^{\frac{CADF-Q}{P}}. \quad \text{(Equation 3)}$$

The content of the fat component contained in an aqueous fluid could be quantified through the CADF value measured by the CADF measurement method according to one embodiment and the Equation 3, which was similar to the values obtained by the GC method. However, the correction constant values used in the Equation 2 were not limited to the correction constants used in the Equation 3.

In one embodiment, the absolute concentration of the fat component in a fat-containing urine sample collected from a liposuction patient by gas chromatography (GC) analysis was measured. Then, the CADFs were measured for the same sample. The correction constants of the Equation 2 were determined through the comparison correction, and the results were compared and shown in FIG. 5. Based on the GC analysis values, the equation for $C_{CADF}$ could be determined as follows, with the correction constants A of 2.03, P of 3.65, Q of 5.53, D of 10, and k, $C_0$ and B of 0:

$$C_{CADF} = 2.03e^{\frac{CADF-5.53}{3.65}}.$$

Figure 6:
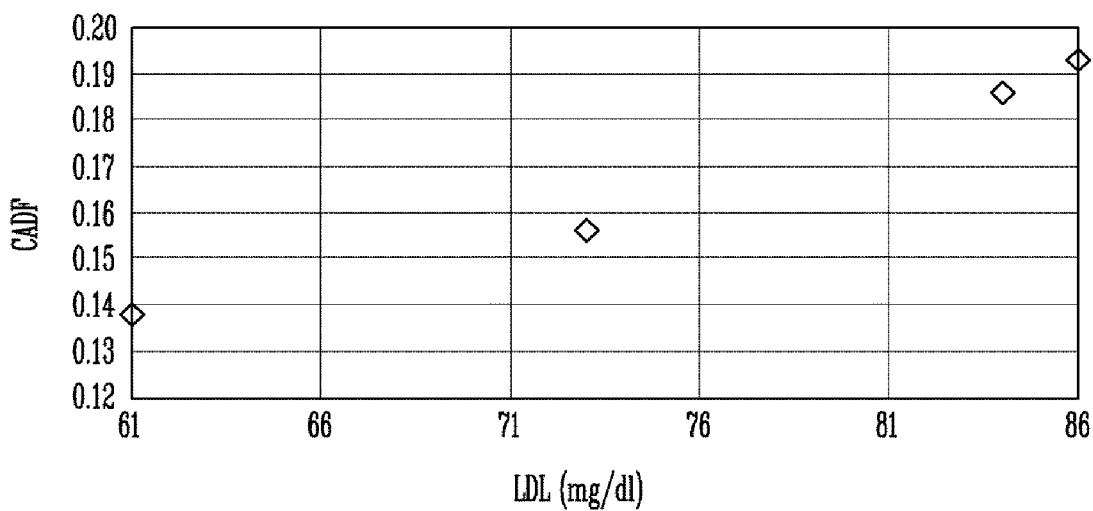
FIG. 6 is a graph showing the relationship between the LDL (low density lipoprotein) values and the CADF values in fat component of a blood sample.

FIG. 6 is a graph showing the relationship between the LDL (low density lipoprotein) values and the CADF values in a blood sample. Referring to FIG. 6, it was confirmed that the LDL value was proportional to CADF, while the HDL value was not correlated with CADF. This showed that the CADF according to one embodiment could be more sensitive to the saturation fat and trans fat which adhere to the blood vessel wall more.

Another embodiment provides a method for providing information about prediction of the possibility of developing a metabolic disease or dementia, or the incidence or progression of a metabolic disease or dementia, using the method for quantifying the content of hydrophobic components contained in a liquid according to one embodiment.

Specifically, a method for providing information about prediction of the possibility of developing a metabolic disease or dementia, or the incidence or progression of a metabolic disease or dementia may comprise the following steps:

(a) contacting a droplet of a body fluid from a subject to a solid surface and measuring an initial contact area ($A_0$) and an initial contact diameter ($d_0$) of the contact surface between the droplet and the solid surface;

(b) after the lapse of predetermined time (t), measuring a contact area ($A_t$) and a contact diameter ($d_t$) of the contact surface;

(c) obtaining a contact area diffusion factor (CADF) according to the following Equation 1;

$$CADF = \left(\frac{A_t^n - A_0^n}{A_0^n}\right)^N + \left(\frac{d_t^m - d_0^m}{d_0^m}\right)^M \quad \text{(Equation 1)}$$

wherein n, m, N and M are constants, (d) obtaining the content of the fat component contained in the droplet by using the contact area diffusion factor (CADF) and the following Equation 2;

$$C_{CADF}(\mu g/ml) = kCADF + C_0 + Ae^{\frac{CADF-Q}{P}} + B\log_D CADF \quad \text{(Equation 2)}$$

wherein k, $C_0$, A, B, D, P and Q are correction constants; and (e) comparing the obtained content of the fat component with the content of the fat component obtained from a body fluid of a normal person.

When the value obtained by subtracting the content of the fat component from the subject from the content of the fat component obtained from the normal person is positive, the possibility of developing the metabolic disease or dementia may be determined as high, or the incidence or progress of the metabolic disease or dementia may be diagnosed.

As used herein, the term 'metabolic disease' may include, but is not limited to, obesity, nonalcoholic liver disease, insulin resistance, hyperinsulinemia, hyperglycemia, diabetes, hypertension, arteriosclerosis, hyperlipidemia or fat embolism, preferably diabetes or fat embolism.

As used herein, the term 'dementia' may include, but is not limited to, Alzheimer's disease, Parkinson's disease, vascular dementia, mixed dementia and mild cognitive disorder.

Figure 7:
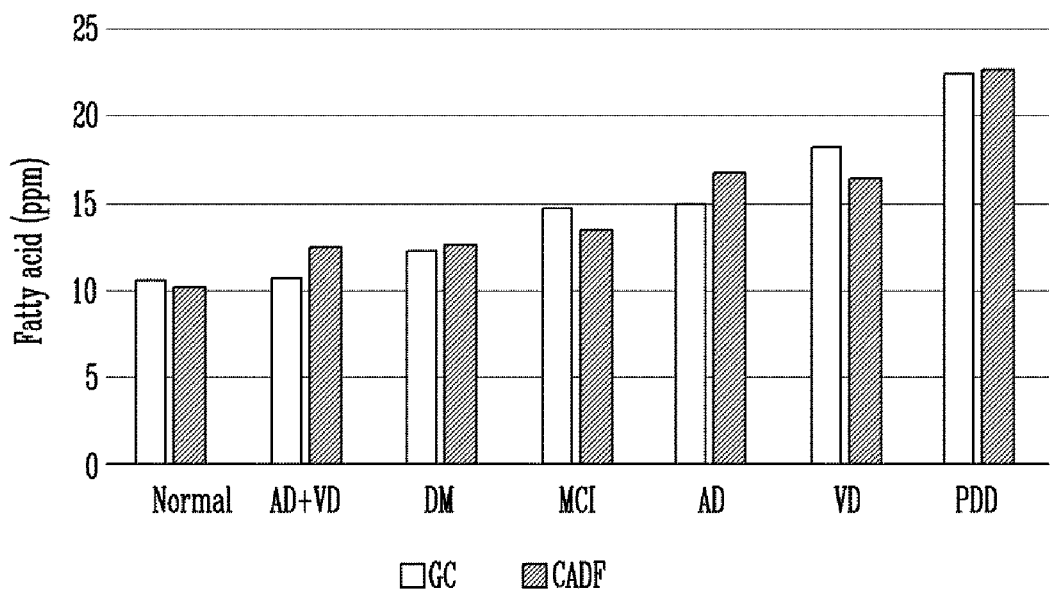
FIG. 7 is a graph comparing the fat component content of urine samples collected from a normal group and six disease patient groups, obtained by the GC method and the CADF method according to one embodiment. Said six diseases are diabetes mellitus (DM), Alzheimer's disease (AD), Parkinson's disease (PDD), vascular dementia (VD), mixed dementia (VD+AD) and mild cognitive disorder (MCI).

FIG. 7 is a graph showing urine free fatty acid pre-clinical test results by comparing the fat component content of urine samples collected from a normal group consisting of one hundred people and six disease patient groups consisting of four hundred people, obtained by the GC method and the CADF method according to one embodiment. Said six diseases are diabetes mellitus (DM), Alzheimer's disease (AD), Parkinson's disease (PDD), vascular dementia (VD), mixed dementia (VD+AD) and mild cognitive disorder (MCI).

Referring to FIG. 7, it was confirmed that the contents of fat components in urine of each patient were much higher than those of the normal person, and both results obtained by the GC and CADF methods were very similar.

In particular, the urine of patients with dementia such as Alzheimer's disease (AD) and Parkinson's disease (PDD) showed a value twice as high as that of the normal person, and it was confirmed that the diagnosis using the CADF method of one embodiment for these diseases was reliable.

In the case of the diabetic patient, the fat component level was lower than that of the dementia patients, but was still higher than that of the normal person. Therefore, the CADF method according to one embodiment could be used as a diabetic diagnostic method. When using the method according to one embodiment, by using urine samples to perform low cost, convenient and consistent diagnosis management, it can greatly help individual diabetes management. The method can also help patients who have difficulty in collecting blood to manage blood sugar.

The method for quantifying the content of the fat component using the CADF method according to one embodiment makes it possible to diagnose dementia by measuring the content of the fatty components in the body fluid which can be easily obtained, such as urine. Therefore, the effects of various dementia treatment methods can be easily compared with each other, and an optimal treatment method for each individual can be found.

When using the method according to one embodiment, it possible to diagnose diabetes by measuring the content of the fatty components in the body fluid which can be easily obtained, such as urine. Therefore, the effects of various diabetes treatment methods can be easily compared with each other, and an optimal treatment method for each individual can be found.

When using the method according to one embodiment, it possible to diagnose and prevent fat embolism by measuring the amount of fat components entering into the blood or urine before, during, or after the liposuction. Therefore, appropriate medical treatment may be given to the patient before the fat embolism appears.

The method for measuring the CADF of one embodiment can be applied to other quantitative analysis techniques, for example, a method for measuring the content of a fat component contained in a sample. Compared to the GC method, the CADF method of one embodiment is fairly cheap, fast and simple.

To complement conventional analytical techniques such as GC, the CADF method of one embodiment may be combined with conventional analytical techniques. For example, a result obtained using the CADF method according to one embodiment can be applied to fat analysis which cannot be directly measured by UV or fluorescence spectroscopy.

The CADF method according to one embodiment can be applied to customized body fat management in the fields of health care, diet, obesity, and the like.

Another embodiment of the present invention provides an apparatus for measuring the concentration of hydrophobic components contained in a liquid, using the method for quantifying the content of hydrophobic components contained in a liquid according to one embodiment.

Figure 8:
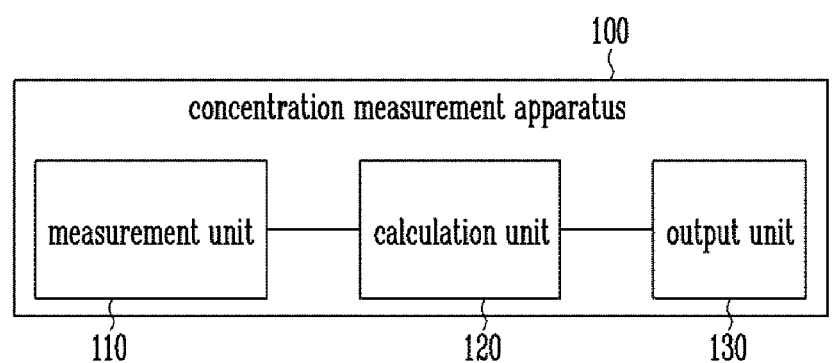
FIG. 8 illustrates an apparatus for measuring the concentration of a hydrophobic component contained in a liquid according to one embodiment.

FIG. 8 illustrates an apparatus for measuring the concentration of a hydrophobic component contained in a liquid according to one embodiment.

Referring to FIG. 8, an apparatus 100 for measuring the concentration of the hydrophobic components contained in the liquid (hereinafter, "concentration measurement apparatus 100") may comprise a measurement unit 110, a calculation unit 120, and an output unit 130. Each component of the concentration measurement apparatus 100 may be implemented in a computing device or in another device operating in conjunction with such a computing device.

The measurement unit 110 may be configured to acquire values of the contact area or the contact diameter with respect to the contact surface of the liquid droplet and the solid surface. The measurement unit 110 may comprise a solid having at least a certain level of a parallel surface where the droplet can be placed.

The measurement unit 110 may comprise an imaging device, such as a CCD (Charge-Coupled Device) camera, an optical sensor, or the like, capable of acquiring images of the droplet and solid for obtaining the values of the contact area or the contact diameter, or a touch sensor provided on the solid surface, but is not limited thereto. The measurement unit 110 may simultaneously measure the contact area or the contact diameter of one or more droplets on the solid surface. The measurement unit 110 may measure different values of the contact area or the contact diameter with time for one liquid droplet.

The measurement unit 110 may comprise an imaging device control unit that can adjust the position, focus, and the like of the imaging device, if necessary. The measurement unit 110 may also comprise a memory which the obtained values of the contact area or the contact diameter may be stored in.

The calculation unit 120 may obtain the CADF according to the following Equation 1 using the obtained values of the contact area or the contact diameter, and the content of the hydrophobic component contained in the droplet may be obtained by calculating with the CADF and the following Equation 2:

$$CADF = \left(\frac{A_t^n - A_0^n}{A_0^n}\right)^N + \left(\frac{d_t^m - d_0^m}{d_0^m}\right)^M \quad \text{(Equation 1)}$$

wherein n, m, N and M are constants, and $$C_{CADF}(\mu g/ml) = kCADF + C_0 + Ae^{\frac{CADF-Q}{P}} + B\log_D CADF \quad \text{(Equation 2)}$$

wherein k, $C_0$, A, B, D, P and Q are correction constants.

The calculation unit 120 may calculate the concentration of the hydrophobic component in the liquid, e.g., body fluids, collected from the subject, based on the concentration data of the hydrophobic component in the liquid collected from the normal person, and may compare the concentrations of the hydrophobic component in the liquids to provide information about prediction for the possibility of developing a metabolic disease or dementia, or information on the incidence or progression of a metabolic disease or dementia.

The output unit 130 may display the concentration of the hydrophobic component, e.g., the fat component, contained in the liquid obtained through the above constructions. In addition, the output unit 130 may display the result of prediction for the possibility of developing the metabolic disease or the dementia, or the information about the incidence or progression of the metabolic disease or the dementia.

By using the method for quantifying the content of the hydrophobic component contained in the liquid according to one embodiment, it is possible to more accurately and simply measure the content of the fat component contained in the sample using a body fluid, such as urine, which can be obtained inexpensively and conveniently from a subject.

Particularly, the quantifying method according to one embodiment may increase the measurement accuracy of the CADF by using both of the contact area and the contact diameter of the droplet as the parameters at the same time. Further, the possibility of measurement errors can be greatly reduced, rather than using only one parameter of the contact area and the contact diameter.

Inventors have mentioned a method for measuring a CADF of a liquid and quantifying fat content penetrated into the liquid using the CADF. The method for measuring the CADF comprises measuring the changes in the contact diameter or the contact area between the droplet and the solid surface over time or measuring the changes in the amount of the fat component present in the liquid to obtain a CADF.

However, since the above CADF measurement method selects one of the contact diameter and the contact area as the measurement variable, there are practical problems to detect the CADF of a liquid accurately.

Particularly, when the initial contact surface between the droplet and the solid does not form a circular shape or when the outer shape of the contact surface changes irregularly after a lapse of a predetermined time, there has been a problem that a measurement error increases with respect to the contact diameter or contact area of the contact surface after a lapse of a predetermined time.

In addition, when the CADF is measured using only the contact area, there is a problem that the boundary line between the droplet and the solid is not identified accurately, in observing the shape of the contact surface in the direction above or below the liquid droplet.

Specifically, in the case of a hydrophobic surface having a contact angle between the droplet and the solid surface of more than 90 degrees, the droplet's outer diameter boundary is larger than the diameter of the contact surface, it is difficult to accurately identify the boundary of the contact surface.

Meanwhile, in the case of a hydrophilic surface with a contact angle between the droplet and the solid surface of less than 90 degrees, the boundary between the droplet and the solid surface is continuously thinned, so that it is difficult to accurately identify the boundary.

In addition, when the CADF is measured using only the contact diameter of the contact surface between the droplet and the solid surface, the shape of the droplet is observed in the lateral direction to discriminate both ends of the contact surface and the distance between the two ends is measured as the contact diameter. However, the shape of the contact surface is often not exactly circular, it is not possible to measure the exact CADF only by the changes in the contact diameter, thereby generating an error. For these reasons, a method for calculating the CADF with improved accuracy by including the contact diameter and the contact area between the droplet and the solid surface as variables has been required, in order to achieve the accuracy of the measurements required to enable practical industrial application.

The present invention has been described above with reference to preferred embodiments thereof. It would be understood by those skilled in the art that various changes in form and details may be made therein without departing from the spirit and scope of the invention as defined by the claims. Therefore, the disclosed embodiments should be considered in an illustrative rather than a restrictive sense. The scope of the present invention is defined by the appended claims rather than the foregoing description, and all changes or modifications derived from the meaning and scope of the claims and equivalents thereof are included in the scope of the present invention.

What I claim is:

1. A method for providing information about prediction of possibility of developing a metabolic disease or dementia, or information about incidence or progression of the metabolic disease or the dementia, comprising:
    (a) contacting a droplet of a body fluid from a subject to a solid surface and measuring an initial contact area ($A_0$) and an initial contact diameter ($d_0$) of a contact surface between the droplet and the solid surface;
    (b) after a lapse of predetermined time (t), measuring a contact area ($A_t$) and a contact diameter ($d_t$) of the contact surface between the droplet and the solid surface;
    (c) quantifying a content of a fat component contained in the droplet based on a contact area diffusion factor (CADF) of the droplet; and
    (d) comparing the quantified content of the fat component with a content of a fat component obtained from a body fluid of a normal person.

2. The method according to claim 1, wherein when a value obtained by subtracting the content of the fat component from the subject from the content of the fat component obtained from the normal person is positive, the possibility of developing the metabolic disease or the dementia is determined as high or the incidence of the metabolic disease or the dementia is diagnosed.

3. The method according to claim 1, wherein the body fluid is selected from the group consisting of blood, serum, plasma, sweat and urine.

4. The method according to claim 1, wherein the metabolic disease is selected from the group consisting of diabetes and fat embolism.

5. The method according to claim 1, wherein the dementia is selected from the group consisting of Alzheimer's disease, Parkinson's disease, vascular dementia, mixed dementia and mild cognitive disorder.

\* \* \* \* \*